United States Patent [19]
Yokoyama et al.

[11] Patent Number: 5,710,099
[45] Date of Patent: Jan. 20, 1998

[54] BIOACTIVE COMPOUNDS

[75] Inventors: Henry Yokoyama, Pasadena, Calif.; Harold W. Gausman, Amarillo, Tex.

[73] Assignee: The United States of America as represented by the Secretary of Agriculture, Washington, D.C.

[21] Appl. No.: 606,791

[22] Filed: Feb. 27, 1996

[51] Int. Cl.$^6$ .......................... A01N 33/04; C07C 217/10
[52] U.S. Cl. .......................... 504/326; 564/346; 564/391; 564/508
[58] Field of Search .......................... 564/346, 391; 504/326

[56] References Cited

U.S. PATENT DOCUMENTS

| | | | |
|---|---|---|---|
| 3,684,530 | 8/1972 | Yokoyama | 99/168 |
| 3,833,350 | 9/1974 | Cooke et al. | 71/98 |
| 3,864,501 | 2/1975 | Yokoyama et al. | 426/268 |
| 3,911,148 | 10/1975 | Yokoyama et al. | 426/268 |
| 3,911,152 | 10/1975 | Yokoyama et al. | 426/268 |
| 4,159,903 | 7/1979 | Bauman | 71/98 |
| 4,204,859 | 5/1980 | Yokoyama et al. | 71/121 |
| 4,322,242 | 3/1982 | Yokoyama et al. | 71/121 |
| 4,363,188 | 12/1982 | Dastoor et al. | 47/58 |
| 4,797,153 | 1/1989 | Yokoyama et al. | 71/121 |
| 5,212,173 | 5/1993 | Kraehling et al. | 514/237.8 |
| 5,298,483 | 3/1994 | Yokoyama et al. | 504/326 |
| 5,304,529 | 4/1994 | Yokoyama et al. | 504/148 |
| 5,324,707 | 6/1994 | Yokoyama et al. | 504/148 |
| 5,583,259 | 12/1996 | Brown et al. | 564/346 |

OTHER PUBLICATIONS

Mndzhoyan et al., Chemical Abstracts, vol. 54, column 13032c.

H.W. Gausman, J.D. Burd, J. Quisenberry, H. Yokoyama, R. Dilbeck and C.R. Benedict, "Effect of 2–Diethylaminoethyl–3,4–Dichlorophenylether (DCPTA) on Cotton Plant (Gossypium hirsutum) Growth and Phenology," *Bio/Technology* 3:255–257 (1985).

H. Yokoyama, C. DeBenedict, W.J. Hsu, and E. Hayman, "Bioregulation of Lipid and Protein Synthesis in Soybean by 2–Diethylaminoethyl–3,4–Dichlorophenlether," *Bio/Technology* 2:712–714 (1984).

J.H. Kiethly and H. Yokoyama, "Regulation of Plant Productivity I: Improved seedling vigor and floral performance of Phalaenopsis by 2–(3,4–dichlorophenoxy)triethylamine [DCPTA]," *Plant Growth Regulation* 9:19–26 (1990).

H. Yokoyama, and J.H. Keithly, "Chemistry of Bioregulatory Agents, Impact on Food Color", *Quality Factors of Fruits and Vegetables: Chemistry Technology,* ACS Symposium Series No. 405, American Chemical Society, (1989) pp. 65–70.

J.H. Keithly, H. Kobayashi and H. Yokoyama, "Effect of 2–(3,4–Dichlorophenoxy) triethylamine (DCPTA) on the Growth and Development of Blue Spruce (Picea Pungens Englm. var. Glauca)," *PGRSA Quarterly* 18:55–61 (1990).

E. Hayman, H. Yokoyama, and S. Gold, "Guayule Cultivar Effect on Rubber Bioinduction," *Journal of Agricultural and Food Chemistry* 35:186–188 (1987).

E. Hayman and H. Yokoyama, "Enhanced Germination Rates and Growth of DCPTA–treated Guayule Seed," *HortScience* 25:1614–1615 (1990).

J.H.Keithly, H. Yokoyama, and H. Gausman, "Enhanced Yield of Tomato in Response to 2–(3,4–dichlorophenoxy) triethylamine (DCPTA)," *Plant Growth Regulation* 9:127–136 (1990).

W.J. Hsu, C. DeBenedict, S.D. Lee, S.M. Poling, and H. Yokoyama, "Preharvest Prevention of Regreening in Valencia Oranges [Citrus sinensis (L.) Osbeck]," *Journal of Agricultural and Food* 37:12–14 (1989).

W.J. Hsu and H. Yokoyama, "Effect of 2–(3,4–Dichlorphenoxy) triethylamine on Tomato *Lycopersicon esculentum* Cv. UCD–82," *Journal of Agricultural and Food Chemistry* 39:96–98 (1991).

H. Yokoyama, S. Gold, C. DeBenedict, and B. Carter, "Bioregulation of Essential Oils of Lemon," *Food Technology* 40:111–113 (1986).

S.M. Poling, W.J. Hsu, and H. Yokoyama, "Synthetic Bioregulators of Poly–Cis Carotenoid Biosynthesis, " *Phytochemistry* 21–601–604 (1982).

S.M. Poling, W.J. Hsu, and H. Yokoyama, "Structure–Activity Relationships of Chemical Inducers of Carotenoid Biosynthesis," *Phytochemistry* 14:1933–1938 (1975).

H. Kobayashi, J.H. Keithly and H. Yokoyama, "Improvements in the Fruit Set and Harvest Index of Eggplant by 2–(3,4–Dichlorophenoxy) triethylamine Hydrochloride [DCPTA]" (*J. Japan. Soc. Hort. Sci*) 60:77–81 (1991).

C.R. Benedict, C.L. Rosenfield, J.R. Mahan, S. Madhavan and H. Yokoyama, "The Chemical Regulation of Carotenoid Biosynthesis in Citrus, " *Plant Science* 41:169–173 (1985).

C.R. Benedict, P.H. Reibach, S. Madhavan, R.V. Stipanovic, J.H. Keithly, and H. Yokoyama, "Effect of 2–(3,4–Dichlorophenoxy)–triethylamine on the Synthesis of cis–Polyisoprene in Guayule Plants (Parthenium argentatum Gray)," *Plant Physiology* 72:897–899 (1983).

G.A. Greenblatt, C.R. Benedict, S. Madhavan and H. Yokoyama, "Crystallographic Analysis of Organic Amine Regulating Carotenoid Synthesis," (Poster 548), *Plant Physiology* 83:134 (1987).

J.H. Keithly, D.P. Jones, and H. Yokoyama, "Survival and Growth of Transplanted Orchid Seedlings Enhanced by DCPTA," *HortScience* 26:1284–1286 (1991).

(List continued on next page.)

Primary Examiner—Richard L. Raymond
Attorney, Agent, or Firm—M. Howard Silverstein; John D. Fado; Margaret A. Connor

[57] ABSTRACT

Novel bioactive compounds which when applied to plants in bioregulatory amounts, enhance plant development responses, resulting in enhanced plant properties such as increased total biomass, increased yield, and increased plant quality. Some of the compounds increase the content of taxol and related taxanes in yew plants. One compound, 2-[diethylaminoethyl]-2-methylpropylether causes plants treated with the compound to have resistance to chewing insects. The compound 2-[diethylaminoethyl]-2-methyl-2-phenylpropylether causes plants treated with the compound to have resistance to sucking insects.

14 Claims, 2 Drawing Sheets

OTHER PUBLICATIONS

H. Yokoyama and J.H. Keithly, "Chemical Agents as Regulators of Biological Responses in Plants," in *Synthesis and Chemistry of Agrochemicals II*, American Chemical Society, pp. 255–268 (1991).

H. Yokoyama and James H. Keithly, "Regulation of Biosynthesis of Carotenoids," *Plant Biochemical Regulators*, Ed H.W. Gausman, Marcel Dekker, Inc., New York, pp. 19–25 (1991).

H. Yokoyama, E.P.Hayman, W.J. Hsu, S.M. Poling, A.J. Bauman, "Chemical Bioinduction of Rubber in Guayule Plant," *Science* 197:1076–1078 (1977).

H. Yokoyama, J.H. Keithly, W.J. Hsu, and E. Hayman, "Chemical Agents as Regulators of Biological Responses in Plants," abstract presented at 193rd ACS National Meeting, American Chemical Society, Denver, CO, Apr. 5–10 (1987).

J.H. Keithly, H. Yokoyama, H.W. Gausman, "Regulation of Crop Growth and Yield by Tertiary Amine Bioregulators," *Plant Biochemical Regulators* Ed. by Harold W. Gausman, Marcel Dekker, Inc., pp. 223–245 (1991).

E.P. Hayman, H. Yokoyama, and K.Z. Bai, "Stimulation of Plant Growth and Gutta Content in Eucommia ulmoides Oliv. by 2–diethylaminoethyl–3,4–dichlorophenylether (DCPTA)," *Plant Growth Regulation* 14:79–82 (1994).

Hideaki Kobayashi, J.H. Keithly and H. Yokoyama, *J. Japan. Soc. Hort. Sci.* 59:115–119 (1990).

H. Yokoyama, S.W. Hsu, S.M. Polin, and E.P. Hayman, "Chemical Regulation of Carotenoid Biosynthesis", In *Carotenoid Chemistry and Biochemistry*, Pergamon Press, Oxford, pp. 371–385 (1982).

H.W. Gausman et al. "Effects of 2–diethylaminoethyl–3,4–dichlorophenylether [DCPTA] on cotton (Gossypium hirsutum L.) Root/Shoot Ratio," *Bull. Plant Growth Regul. Society Am.* 16:6–7 (1988).

K.D. Sanderson, H. Yokoyama, W.D. Hearn, "Effect of Prepropagation Immersion of Cuttings in DCPTA on Growth and Flowering Chrysanthemums," *Bull. Plant Growth Regul. Soc. Am.* 16:8–9 (1988).

BIOACTIVE COMPOUNDS

BACKGROUND OF THE INVENTION

1. Field of the Invention

The present invention relates to and has among its objects the provision of novel bioactive compounds. In one aspect of the invention, the compounds are plant biochemical regulators which are useful for enhancing plant growth including increasing total plant biomass and important plant constituents thereby increasing crop yield and plant quality. In another aspect, selected compounds are useful to increase the content of taxol and related taxanes in yew plants. In another aspect, selected compounds are useful to elicit resistance in plants to sucking or chewing insects.

2. Description of the Art

Advancements in agriculture have led to the development of chemical compounds and methods for their application as plant bioregulators to enhance one or more constituents of the treated plant. For example, U.S. Pat. No. 3,671,219 discloses a process for increasing the sucrose yield of sugarcane by treating sugarcane a few weeks prior to harvest with a quaternary ammonium salt which is a benzyl dimethyl alkyl or substituted alkyl ammonium halide. U.S. Pat. No. 3,833,350 describes a method of inducing carotenoid synthesis or accumulation in plants, fruits, and vegetables, by treating the plants just before or after harvest with a halogenated phenoxytriethylamine or halogenated phenylthiotriethylamine. U.S. Pat. Nos. 3,684,530; 3,864,501; 3,911,148, and 3,911,152 disclose methods for increasing the carotenoid pigment of fruits and vegetables by treating the surface of harvested fruits or vegetables with compounds including substituted 2-(p-diethylaminoethyloxybenzal) acetone or (substituted phenoxy) trialkylamines.

U.S. Pat. Nos. 4,204,859 and 4,322,242 describe a method for increasing rubber hydrocarbons in guayule and Hevea rubber plants by application of certain substituted phenoxytrialkylamines to 4 or 8-month old plants. U.S. Pat. No. 4,159,903 discloses a method for increasing polyisoprene production in rubber producing plants such as guayule by application of substituted trialkylamines. U.S. Pat. No. 4,363,188 describes a method of stimulating the in vitro propagation of polyisoprene containing plants from a nutrient medium by the addition of certain substituted trialkyl amines to the medium.

U.S. Pat. No. 4,797,153 discloses a method for increasing total plant biomass and individual plant constituents such as protein, lipid, sugar, and essentials oils by application of certain substituted phenoxytrialkylamines and substituted phenylthiotrialkyl amines or akalkylmorpholium halides. The compounds are applied in bioregulatory amounts to plants at an early state of plant development, for example, to seeds, plant seedlings, or plant buds, or to trees during flower bud swell.

U.S. Pat. Nos. 5,298,483; 5,304,529, and 5,324,707 describe methods for enhancing plant growth by treating plants at an early stage of plant development with a bioregulatory amount of one or more (benzyl substituted) trialkylamine ether compounds. The enhanced plant growth includes increases in photosynthesis, total plant biomass, and plant constituents including increases in vitamin C, carotenoids, and essential oil contents of citrus fruit.

SUMMARY OF THE INVENTION

The present invention is directed towards two new classes of novel bioactive compounds. The first class comprises 2-[diethylaminoethyl]-2-methylpropyl ethers shown in Group I, below. The second class comprises 2-[N-methylbenzylaminoethyl] substituted ether compounds shown in Groups II–IV, below. The compounds in all groups have activity as plant biochemical regulators, and when applied to plants in bioregulatory amounts, they elicit superior biological responses in plants at very low levels of concentration, including increase in total plant biomass, increase in yield, and increase in crop quality. In addition, some of the novel bioactive compounds stimulate synthesis of taxol and related taxanes in yew plants. One compound, 2-[diethylaminoethyl]-2-methylpropylether causes plants treated with the compound to have resistance to chewing insects. The compound 2-[diethylaminoethyl]-2-methyl-2-phenylpropylether causes plants treated with the compound to have resistance to sucking insects.

The compounds of the invention may be categorized as follows:

Group I. 2-[Diethylaminoethyl]-2-methylpropylethers of the structure

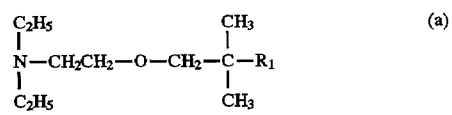

wherein $R_1$ is hydrogen, methyl or phenyl; or (b) an acid addition salt of the compounds of (a).

Group II. 2-[N-Methylbenzylaminoethyl]-2-methylpropylethers of the structure

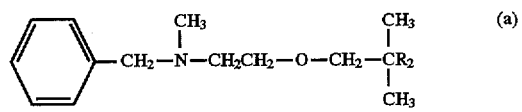

wherein $R_2$ is hydrogen or methyl; or (b) an acid addition salt of the compounds of (a).

Group III. 2-[N-Methylbenzylaminoethyl]benzylethers of the structure

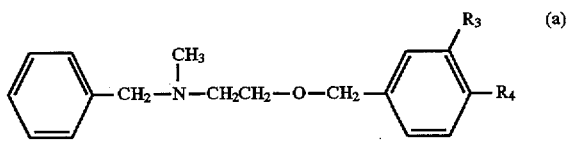

wherein $R_3$ and $R_4$ are in the mere and para positions, respectively, on the ring, and wherein $R_3$ is hydrogen or methyl and $R_4$ is methyl, or wherein $R_3$ and $R_4$ are both chlorine; or (b) an acid addition salt of the compounds of (a).

Group IV. 2-[N-Methylbenzylaminoethyl]-2-methyl-2-phenylpropylether of the structure

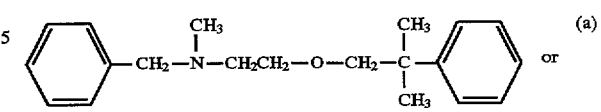

(b) an acid addition salt of the compound of (a).

In one aspect of the invention the compounds are used as plant bioregulator compounds for enhancing plant growth including increasing total plant biomass and important plant constituents thereby increasing crop yield and plant quality. The compounds are applied in effective bioregulatory amounts, this is, an amount sufficient to increase total plant biomass but insufficient to inhibit plant growth. Application is carried out at an early stage of plant development, that is, to the seed or to a plant or plant part during the active cell division stage of plant development. It has been found that the application of the compounds of the invention causes the treated plants to form and store valuable plant constituents over that of untreated plants. Thus plants which have been treated with the bioregulatory compounds of the invention have greater total biomass than untreated plants resulting in increased agricultural crop production per unit area. Moreover, increases in photosynthesis and increases in important plant constituents such as protein, lipid, sugar, carotenoid content, plant waxes and essential oil content are observed in treated plants that produce the same, compared to untreated control plants. Pigment accumulation in plant leaves and fruits is increased. Increases in seed and flower yields have also been observed.

Further, enhanced plant growth is demonstrated by increases in total soluble solids, vitamin or nutrient contents of fruits harvested from treated plants compared to untreated controls.

In most cases the invention increases the growth rate of the treated plant relative to untreated plants, resulting in accelerated maturation. Shorter growing periods effect a decrease in the labor and cost of production and effect a decrease in the use of energy sources such as fossil fuel which are used in fertilizer production. Moreover, accelerated and increased growth make likely the possibility that growing cycles will be shorter while yielding a harvest equivalent or superior to that of untreated plants. Such a harvest would be greater since the treated plants exhibit increased biomass. It is even conceivable that multiple harvests can be achieved within growing seasons. These possibilities offer promise for increased food productions at reduced costs to alleviate food shortages throughout the world.

Another aspect of the invention is application of selected compounds to increase the content of taxol and related taxanes in yew plants.

Another aspect of the present invention is application of selected compounds to elicit resistance in plants to sucking or chewing insects.

DETAILED DESCRIPTION OF THE INVENTION

Figure 1:
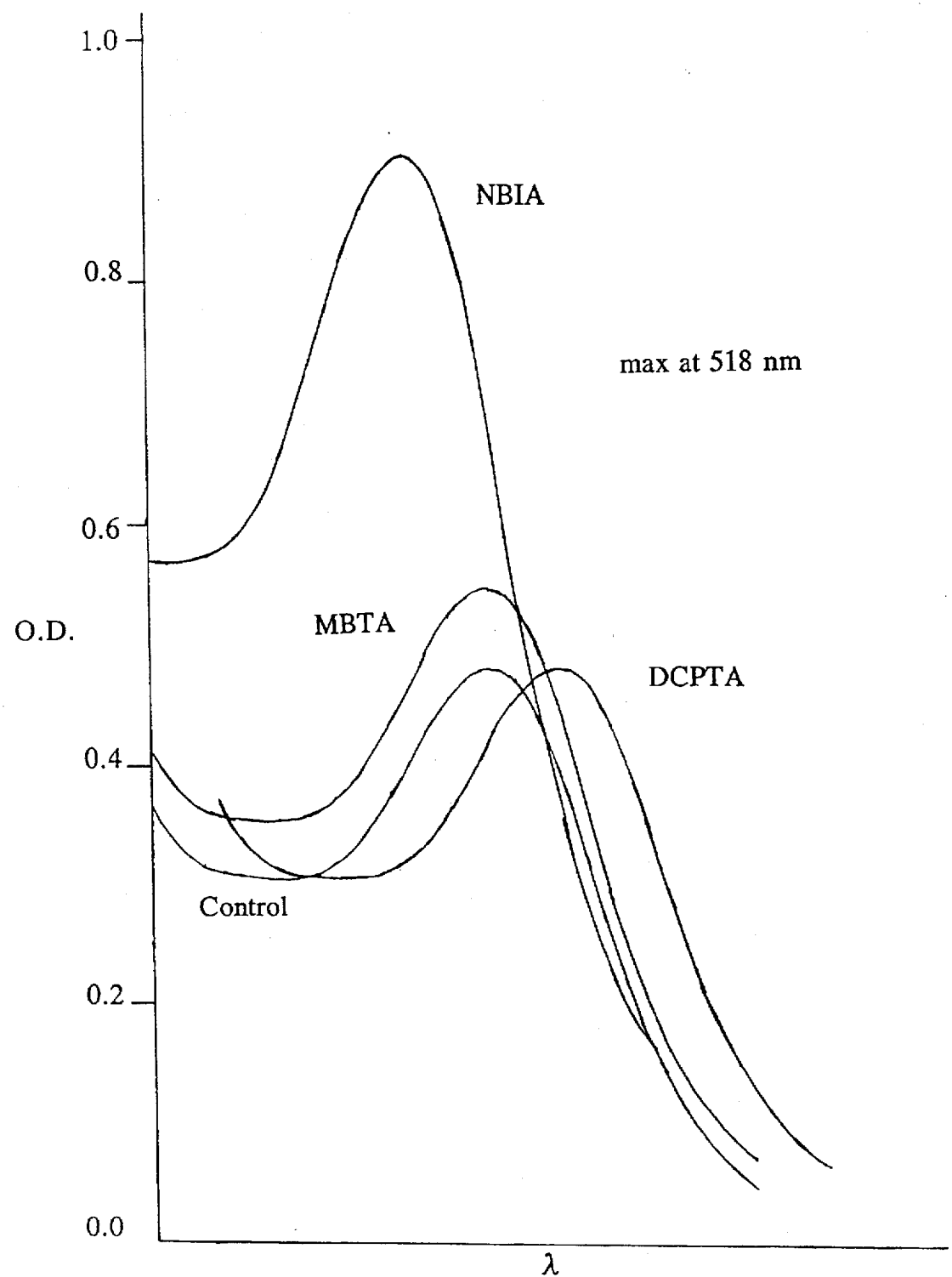
FIG. 1 shows the visible spectra of extracts of anthocyanin pigments from Red Flame seedless grapes treated with the compound of the invention, 2-[N-methylbenzylaminoethyl]-2-methylpropylether (NBIA), the prior art bioregulators DCPTA and MBTA, and control. The y-axis is optical density (O.D.). The x-axis is wavelength ($\lambda$) in rim. The absorption maximum ($\lambda_{max}$) for each curve is at 518 nm.

In one aspect of the invention, the compounds of the invention are plant biochemical regulators. The compounds effect plant biomass development and plant constituent formation. In most cases, earlier crop maturation is observed. The compounds significantly increase plant biomass, crop yield, and yield quality. Pigment accumulation in plant leaves and mature fruits is increased. The bioregulatory benefits of the invention are obtained by applying any of the compounds of the invention in an effective bioregulatory amount to plants at an early stage of plant development such as to plants seeds, plant seedlings, plant buds or immature fruits.

Without any intention of limiting the scope of the invention, it is theorized that the compounds used in the method of the invention play a role in the photosynthetic pathway in green plants. It is theorized that application of the compounds to the developing green plant causes increased fixation of carbon dioxide in the photosynthetic pathway thereby increasing the carbon atoms available for synthesis of total biomass and individual plant constituents. It is further theorized that use of the compounds at an early stage of plant or fruit development and before completion of cell differentiation manipulates the genetic expression of the plant so as to tap unused biological potential. Thus as new cells develop under the influence of the bioregulatory compounds, they possess increased capacity to form and store valuable materials and to form increased amount of plant tissues. The combination of enhanced photosynthate supply and enhanced photosynthate utilization appears to maintain positive and balanced correlations between crop yield and yield quality. No negative imbalances appear to be observed.

Examples, by way of illustration and not limitation, of compounds of the invention are:

Group I. 2-[Diethylaminoethyl]-2-methyl-2-substituted propyl ethers wherein the 2-substituent is hydrogen, phenyl or methyl.

Group II. 2-[N-Methylbenzylaminoethyl]-2-methyl-2-substituted propyl ethers wherein the 2-substitutent is hydrogen or methyl.

Group III. 2-[N-Methylbenzylaminoethyl] substituted benzyl ethers wherein the substituents are in the meta and para positions, respectively, on the phenyl ring, and wherein the meta substituent is hydrogen or methyl and the para substituent is methyl, or wherein the meta and para substituents are both chlorine.

Group IV. 2-[N-Methylbenzylaminoethyl]-2-methyl-2-phenylpropyl ether.

The invention also encompasses the acid addition salts of the compounds of the invention.

The ether compounds of the invention are prepared using commercially available starting materials. The appropriate alcohol is refluxed with sodium metal to yield the sodium alkoxide. The appropriate substituted alkyl chloro or bromo halide is added to the sodium alkoxide, and the mixture is refluxed to obtain the ether compound of the invention. The sodium halide byproduct is removed by filtration or other means known in the art. Acid addition salts of the ether are readily produced by the addition of an acid, for example, hydrochloric acid, as is known in the art.

The synthesis of the ethers of the invention is illustrated as follows:

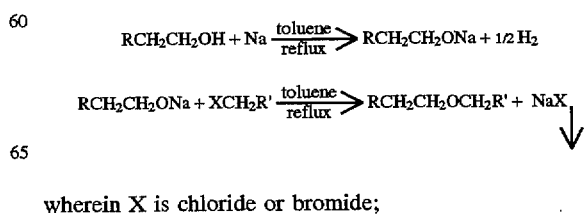

wherein X is chloride or bromide;

wherein R is:
Group I: $(C_2H_5)_2N$—
Groups II–IV:

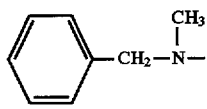

wherein R' is:
Group I: —$C(CH_3)_2R_1$
Group II: —$C(CH_3)_2R_2$

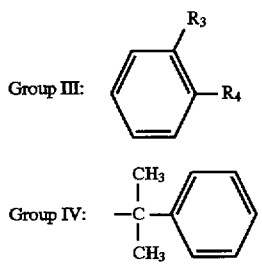

wherein $R_1$, $R_2$, $R_3$ and $R_4$ are as defined above.

Exemplary of the synthesis of the compounds of the invention is the synthesis of 2-[N-methylbenzylaminoethyl]-2-methylpropylether, which is described in detail in Example 1, below.

The acid addition product is conveniently prepared by adding acid to the ether as known to those in the art.

Purification of the free amine is conveniently carried out by vacuum distillation. Purification of the acid addition salt is conveniently carried out by crystallization.

To obtain plant bioregulator effects, the compounds are applied during the active cell division stage of plant development. Only one application is needed for effecting plant responses. We have found that about 3–4 weeks after application even trace amounts of the bioregulator of the invention cannot be detected in the plant tissues. The bioregulator disappears, yet the effects are already established in the young plant cells. Application at the active cell division stage is the critical feature for transmittal of the bioinduced regulatory gene expression information from one cell to another. Treatment protocols include seed treatment and foliar application at the early seedling stage of growth, that is, shortly after germination and seedling emergence and during stages of active cell division of the plant, for example, at the 2–4 true leaf stage. Responses are drastically reduced when foliar application is made after active cell division has ceased and application made during cell elongation stage. The foregoing treatment protocols are especially useful for annual crops including dicots and monocots and floral plants and ornamentals. Exemplary dicots are tomato, radish, sugarbeet, and cotton. Exemplary monocots are wheat, corn, barley, oats, and grasses.

For vine-grown crops, application is made during stages of active development of the shoots, preferably shortly after shoot emergence. Treatment at a later stage of berry set results in minimal responses. For example, on deciduous fruit vines such as grapes, application should be made shortly after shoot emergence (2–5 cm); applications at time of berry blossom/berry set are too late.

For tree-grown crops, application is made during the early stages of active development of the fruit, for example, during flower bud swell or shortly after the opening of the bud. Conveniently, application may be made a week before or after flower bud swell. For citrus trees, application can be made at the flower bud swell as described above; application can also be made a week before or during fruit development when the fruit cells are in the active cell division stage and before maturity into the cell elongation stage, that is, when the fruits are not more than about 0.5–1.5 cm in diameter. On nondeciduous fruit trees such as citrus, it is preferred that application be made at blossom time or no later than shortly after fruit set. On deciduous fruit trees such as peaches, apricots, and nectarines, it is preferred that application be made at blossom time or no later than at fruit set and emergence of shoots/leaves.

On floral plants such as pansy, petunia, geranium, and carnation, applications are carried out at early seedling stage (3–5 leaf stages) or seed soak (3–8 hours, depending on ease of solution uptake). For other floral plants such as tulips, the bulbs can be soaked overnight prior to cold treatment/conditioning and planting.

For vegetatively propagated plants like sugarcane, or shrubs such as Candelilla, application should be made at the developmental growth stages equivalent to the ones aforementioned.

To obtain plant bioregulator effects, the compounds of the invention are applied in an effective bioregulator amount, that is, an amount effective to increase plant biomass but insufficient to inhibit growth of the plant.

The compounds of the invention have activity at low concentration. Treatment is conveniently applied by seed treatment or foliar application. Treatment rates are about 0.0125 to 10 parts per million (ppm).

Generally, where the compounds are applied to the seeds, the concentration is about 0.001 to 0.01 mg of active ingredient per seed. Application is conveniently made by dissolving the compound or the acid salt in water with a water-wetting agent solution (0.05 to 0.1% of wetting agent) at a concentration of 0.01 to 10 ppm in the diluent and soaking the seeds for 3 to 8 hours. Other means of treatment of seeds such as encapsulation of the seeds with the compounds by conventional methods are encompassed by the invention.

On transplanting of seedlings, root soak techniques may be employed. Generally the roots of the seedlings are soaked in about 0.1 to 10 ppm of the bioregulator solution from about 5–30 minutes. Soaking time in a particular instance is determined by ease in which the bioregulator is taken up by the roots. The seedlings are transplanted after root soak without drying.

When foliar application is made to the seedling at the 2–4 leaf stage, the treatment is about 0.001 to 0.1 mg active ingredient per plant. This can be accomplished by using a treatment rate of about 0.0125 to 10 ppm. The plants are sprayed until drip-off. The specific amount in a particular instance depends on several factors such as size of the plant, how broad the leaves are, type of plant, e.g., monocot or dicot. Generally 10–15 ml of the treatment solution is sufficient.

Appropriate wetting agents and penetrating agents such as polyoxyethylene (20) sorbitan monooleate (Tween 80) and Kinetic™, a nonionic wetter/spreader/penetrant/adjuvant [proprietory blend of polyalkyleneoxide modified polydimethylsiloxane and organosilicane surfactants] (Helena Chemical Company, Phoenix, Ariz.) as known in the art may be added to aid in plant treatment.

As stated above, the compounds of the invention when applied in accordance with the method of the invention, substantially increase total biomass, enhance the amount of some or all plant constituents and in many cases increase the rate of growth in green plants over untreated plants as long as constituents such as water and light which are necessary for plant growth are present in the required amount. For example, increases in photosynthesis and increases in important plant constituents such as protein, lipid, sugar, carotenoid content, plant waxes and essential oil content are observed in treated plants that produce the same, compared to untreated control plants. Pigment accumulation in plant leaves and fruits is increased. Increases in seed and flower yields have also been observed. Further, enhanced plant growth is demonstrated by increases in total soluble solids, vitamin or nutrient contents of fruits harvested from treated plants compared to untreated controls. In most cases the invention increases the growth rate of the treated plant relative to untreated plants, resulting in accelerated maturation.

It has been found that in studies conducted wherein the compounds were compared with the bioregulator compounds disclosed in U.S. Pat. No. 4,797,153, specifically 3,4-dichlorophenoxytriethylamine (2-[diethylaminoethyl]-3,4-dichlorophenylether) (DCPTA) and the bioregulator compound disclosed in U.S. Pat. No. 5,298,483, specifically 2-[diethylaminoethyl]-4-methylbenzylether (N,N-diethylaminoethyl(4-methylbenzyl)ether) (MBTA), it was determined that compounds of the present invention are generally more effective as plant bioregulators than the bioregulator compounds disclosed in the '153 or '483 patents. For example, as shown in Example 4, below, application of the novel bioactive compounds at 1 ppm increased biomass in radish plants 28 to 98% compared to plants treated with DCPTA, and increased biomass 21 to 97% compared to MBTA. The superior nature of the new compounds is observed in the comparison of increases of fresh radish root weight ranging from 17% to 193% when compared to DCPTA at the 1 ppm concentration and 18% and 194% when compared to MBTA. The novel bioactive compound, 2-[N-methylbenzylaminoethyl]-4-methylbenzylether at the low level of 0.1 ppm increased biomass and root weight by 86% and 177% compared to untreated controls. In contrast, DCPTA and MBTA were ineffective at the 0.1 ppm level.

The superior performance of the compounds of the invention over DCPTA and MBTA is also illustrated in FIG. 1 (see Example 10 below), and Examples 12-14, below. Thus, the compounds of the invention exhibit a structure-activity correlation superior to the disclosed prior art and thus represent an advance in the state of the art of bioregulators.

Selected novel bioactive compounds of the invention increase the content of taxol and related taxanes in yew plants including *Taxus baccatta*, *Taxus brevifolia*, T. sp. x T. media cv. Hicksii, and *Taxus cuspidata*. The compounds are Group I compound wherein $R_1$ is hydrogen; Group II compound where $R_2$ is hydrogen; Group III compounds, particularly N-methyl-2-benzylaminoethyl-4-methylbenzylether and 3,4-dimethylbenzylether and 3,4-dichlorobenzylether analogs; or acid addition salts of the foregoing compounds The compounds are applied in effective amounts, that is, an amount sufficient to increase taxol and related taxanes but insufficient to inhibit growth of the yew plant. Related taxanes include taxol precursors, e.g., 3,10-deacetylbaccattin-III and taxol analogs, e.g., baccattin-III.

Application is carried out at an early stage of plant development, that is, to the seed or to a plant seedling, or plant part (clone). The compounds have activity at low concentration. Treatment is conveniently applied by seed treatment, seedling root soak or foliar application. Treatment rates are about 1 to 10 ppm.

One useful technique employed is to treat roots of seedlings propagated from clones (cuttings). Seedlings are treated by soaking roots in the bioregulator solution such as 1, 5, 10 ppm with a wetting agent, e.g., 0.1% Kinetic™ for 10 to 20 minutes and transplanting without drying. Seed treatment is carried out by soaking seeds in the bioregulator solution (1 to 10 ppm) with a wetting agent, e.g., 0.1% Kinetic™.

As shown in Example 16, below, application of the novel bioactive compounds increased taxol content in yew plants 112 to 175% and increased biomass by 33 to 41% compared to control plants. Increases of 25 to 27% taxol content and 10 to 15% biomass were observed in yew plants treated with the novel bioactive compounds compared to plants treated with DCPTA. These increases in taxol were observed throughout the above ground portion of the plant, e.g., stems, branches, and needles.

This application provides an important means of enhancing the production of the important anticancer drug taxol from natural sources.

Selected compounds are useful to elicit resistance in plants to sucking or chewing insects. The compound 2-[diethylaminoethyl]-2-methylpropylether causes plants treated with the compound to have resistance to chewing insects. The compound 2-[diethylaminoethyl]-2-methyl-2-phenylpropylether causes plants treated with the compound to have resistance to sucking insects. Surprisingly, while the compounds in themselves do not have pesticidal properties, they elicit resistance in plants to insects.

Examples of chewing insects are cabbage looper, tobacco horn worm, and potato beetle. Examples of sucking insects are aphids, sweet potato whitefly, and silverleaf whitefly.

The compounds are applied in effective resistance-eliciting amounts, that is, an amount sufficient to cause resistance by the plant to the selected insect, but insufficient to inhibit growth of the plant. Seed soak rather than foliar treatment is the preferred treatment. Seed soak affords immediate protection to emerging seedlings whereas foliar treatment exposes young seedlings to insect damage before treatment takes effect. For example, tomato seeds are soaked in the bioregulator solution at a concentration of about 1 to 10 ppm in a wetting agent, e.g., 0.1% Kinetic™ for 6-8 hours. Treated seeds are planted without drying.

This application is illustrated in Examples 17 and 18, below.

EXAMPLES

The following examples are intended only to further illustrate the invention and are not intended to limit the scope of the invention which is defined by the claims.

Example 1

This example describes the synthesis of the compounds of the invention. Exemplary is the synthesis of 2-[N-methylbenzylaminoethyl]-2-methylpropylether.

One hundred grams of N-methyl-N-benzylethanolamine were added to 14 grams of sodium in toluene and refluxed with gentle stirring for about 3 hours or until all the sodium had reacted or dissolved. To this reaction mixture were slowly added 84 grams of isobutylbromide in 100 ml toluene. The whole reaction mixture was refluxed with gentle stirring for an additional 6 hours and allowed to cool to room temperature. The precipitated sodium bromide was removed by filtration. The filtrate was washed three times with equal volumes of water, and then the toluene removed using a rotary evaporator. The residue was taken up in 200 ml diethylether, and the solution was cooled in an ice bath. One hundred grams of ice were added to the cooled solution. Five hundred ml of 20 % HCl (previously cooled in an ice bath) were added to the reaction product and stirred 1 hour. The diethylether was allowed to evaporate at room temperature. The residue was taken up in 100 ml isopropyl alcohol and placed in an ice bath or cold room for crystallization. Recrystallization two times yielded 80 grams of product.

The acid addition product was prepared by adding hydrochloride acid to the ether product with stirring. Purification was carded out by recrystallization.

Example 2

This example sets forth the structures and $^{13}$CNMR data for six of the compounds of the invention. The $^{13}$CNMR data were determined on the hydrochloric acid addition salts of the compounds in $D_2O$ using a JEOL-270 spectrometer in the FT mode, 60 min., concentration: 50 mg/2ml.

Group I

2-[Diethylaminoethyl]-2-methylpropylether (IBTA). $^{13}$CNMR (67.8 MHz, $D_2O$) 8.6, 18.9, 27.8, 48.0, 48.3, 51.5, 64.5.

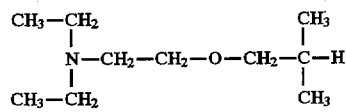

2-[Diethylaminoethyl]-2-methyl-2-phenylpropylether (PBTA). $^{13}$CNMR (67.8 MHz, D20) 8.7, 20.7, 24.2, 40.6, 48.6, 55.0, 67.2, 129.1, 130.0, 130.6, 131.4.

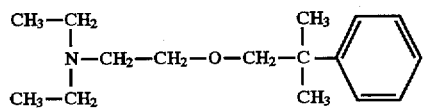

Group II

2-[N-Methylbenzylaminoethyl]-2-methylpropylether (NBIA). $^{13}$CNMR (67.8 MHz, $D_2O$) 20.7, 29.7, 42.5, 56.7, 62.2, 66.1, 80.2, 131.1,131.6, 132.4, 133.1.

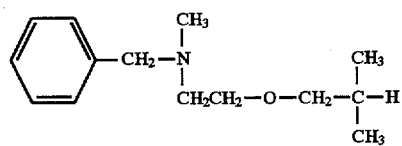

Group III

2-[N-Methylbenzylaminoethyl]-4-methylbenzylether (NBMA). $^{13}$CNMR (67.8 MHz, $D_2O$) 20.2, 41.6, 54.4, 62.6, 64.2, 79.2, 130.1, 130.2, 130.8, 131.2, 131.8, 132.2, 133.2, 133.6. 2-[N-Methylbenzylaminoethyl]-4-methylbenzylether in the hydrochloride form (water soluble) is extremely hygroscopic and must be stored with a desiccant. The crystalline material must be handled under dry atmospheric conditions.

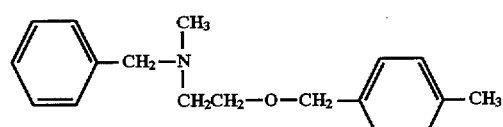

2-[N-Methylbenzylaminoethyl]-3,4-dimethylbenzylether (NBDA). $^{13}$CNMR (67.8 MHz, $D_2O$) 20.2, 21.6, 41.5, 52.1, 62.8, 63.2, 79.1, 130.6, 130.7, 130.9, 131.1, 131.2, 131.2, 132.6, 133.1, 133.2, 133.6.

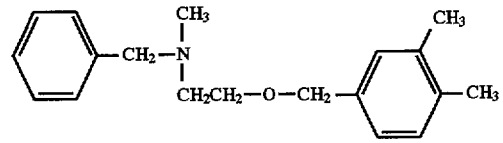

Group IV

2-[N-Methylbenzylaminoethyl]-2-methyl-2-phenylpropylether (NBPA). $^{13}$CNMR (67.8 MHz, $D_2O$) 20.1, 24.6, 42.5, 56.7, 62.1, 66.1, 80.1, 129.1, 129.6, 130.8, 131.2, 131.7, 131.7, 132.1, 132.6.

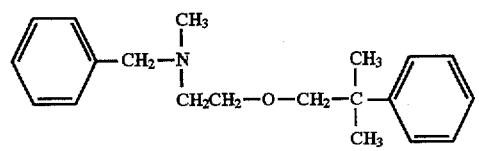

Example 3

This example describes the plant bioregulator effects of a compound of the invention using two different wetting agents. Solutions of the hydrochloric acid salt of 2-[diethylaminoethyl]-2-methylpropylether (10 ppm active ingredient) in 0.1% wetting agent in water were prepared using polyoxyethylene (20) sorbitan monooleate (Tween 80 from Sigma Chemicals) or Kinetic™ (proprietory blend of polyalkyleneoxide modified polydimethylsiloxane and organosilicane surfactants from Helena Chemical Company, Phoenix, Ariz.). The bioregulator solutions were applied to table radish [*Raphanus sativus* cv. Champion] at the 2–3 leaf state to foliage runoff. Control plants were treated the same as the test plants except that no bioregulator compound was used. The solution applied to control plants was 0.1% wetting agent. Six replicates of the test and control plants were carried out for each wetting agent. The plants were harvested 31 days after planting, and the biomass [fresh weight (gm)] of each plant was measured.

Results. The effect of the plant bioregulator compound of the invention on radish biomass using different wetting agents is shown in Table 1. In both cases, biomass was increased significantly over the control. However, even though uniform wetting was observed with both wetting agents, increased biomass amounts were obtained using bioregulator in Kinetic™ compared to bioregulator in Tween 80.

TABLE 1

| Radish Biomass Fresh Weight (gm) | | | |
|---|---|---|---|
| Kinetic ™ | | Tween 80 | |
| Compound[1] | Control 2 | Compound[1] | Control 2 |
| 50.6 | 21.4 | 34.5 | 22.8 |
| 50.4 | 23.1 | 32.7 | 19.7 |
| 51.0 | 19.7 | 33.3 | 21.1 |
| 51.2 | 22.4 | 31.3 | 18.4 |
| 50.1 | 18.8 | 32.2 | 20.7 |
| 49.1 | 23.9 | 32.6 | 19.3 |

[1]10 ppm 2-[diethylaminoethyl]-2-methylpropylether in 0.1% wetting agent.
[2]0.1% wetting agent.

Example 4

This example describes bioregulator effects of the compounds of the invention on radish plants.

The hydrochloric acid salts of the following compounds were prepared as described above:

2-[diethylaminoethyl]-2-methylpropylether (IBTA);
2-[diethylaminoethyl]-2-methyl-2-phenylpropylether (PBTA);
2-[N-methylbenzylaminoethyl]-2-methylpropylether (NBIA);
2-[N-methylbenzylaminoethyl]-4-methylbenzylether (NBMA);
2-[N-methylbenzylaminoethyl]-3,4-dimethylbenzylether (NBDA);
2-[N-methylbenzylaminoethyl]-2-methyl-2-phenylpropylether (NBPA).

Aqueous solutions containing the bioregulator acid salts (10, 1, or 0.1 ppm active ingredient) and 0.1% Kinetic™ were prepared. The bioregulator solutions were applied in a single application per treatment to table radish [*Raphanus sativus* cv. Red Devil B] at early seedling (2–3 leaf) stage to foliage runoff (10 ml/plant) as a foliar application. For purposes of comparison, applications of known bioregulators, 2-[diethylaminoethyl]-3,4-dichlorophenylether (DCPTA) and 2-[diethylaminoethyl]-4-methylbenzylether (MBTA), were carried out as described above. Control plants were treated as described above using 0.1% Kinetic™ wetting agent and no bioregulator.

The plants were grown in 1 gallon pots in the greenhouse. Six replicates of the test treatments, comparison treatments, and controls were carried out. The experimental pots were arranged randomly.

The plants were observed during the growing period to assess differences between the test treatments, comparison treatments, and controls. The plants were harvested 32 days after planting.

The wet (fresh) weight yields of total biomass (whole plant) and roots were measured. To obtain the root weight, the roots were separated from the leaves and stems and weighed without prior drying, i.e., wet weights. The anthocyanin pigment content of the plants was determined as follows: taproots were freeze-dried, weighed, and extracted with methanol. Absorbance readings were taken on the spectrophotometer at 520 nm and correlated to amount.

Results. Increase in green color of the leaves of the test radish plants over the control plants and plants treated with comparison bioregulators was noticeable within a week after application of the compounds of the invention and comparison bioregulators, reflecting an increase in the chlorophyll content. The test radishes attained a deeper red coloration than the controls and plants treated with comparison bioregulators, indicating an increase in the anthocyanin pigment content. The foliage of the test plants was somewhat larger and more upright at a steeper angle than the controls.

As seen in Table 2, application of the compounds of the invention increased biomass root weight and anthocyanin pigment content (color) over the controls and comparison bioregulators. Overall, the increases in biomass exhibited by the new compounds ranged from 19% (1.2-fold) to 93% (1.9-fold) compared to control plants. Several of the novel bioactive compounds (IBTA, PBTA, NBMA) were most effective at 1 ppm and increased biomass ranging from 36% (1.4-fold) for PBTA to 93% (1.9-fold) for NBMA when compared to control plants; also NBMA increased biomass 86% (1.8-fold) at the even lower concentration level of 0.1 ppm. Both DCPTA and MBTA were completely ineffective at 0.1 ppm level. At the 10 ppm level, biomass increases ranged from 23% (1.2-fold) for NBPA to 56% (1.6-fold) for NBIA compared to control plants.

All of the novel bioactive compounds exhibited superior properties over either DCPTA or MBTA. At the 1 ppm concentration level, biomass increases ranged from 21% (1.2-fold) for NBPA to 98% (2-fold) for NBMA when compared to DCPTA and 21% (1.2-fold) to 97% (2-fold) when compared to MBTA. At the 10 ppm, biomass increases ranged from 10% for NBPA to 41% for NBIA when compared to DCPTA and 7% for NBPA to 37% for NBIA.

Overall, increases in fresh root weight shown by the novel bioactive compounds ranged from 14% for NBIA to 183% for NBMA when compared to the controls and these results were observed at the 1 ppm concentration level; even at the lower level of 0.1 ppm NBMA showed a 177% increase in root weight. At the 10 ppm concentration level, increases in root weight ranged from 36% for NBPA to 73% for IBTA when compared to control plants.

The superior nature of the new compounds is observed in the comparison of increases of fresh radish root weight ranging from 17% for NBIA to 193% for NBMA when compared to DCPTA at the 1 ppm concentration and 18% and 194%, respectively, when compared to MBTA. Again, both DCPTA and MBTA were completely ineffective at the 0.1 ppm level. At the 10 ppm level, fresh root increases ranged from 23.6% (1.2-fold) for NBPA to 57.1% (1.6-fold) for IBTA when compared to DCPTA and 15.0% (1.2-fold) to 46.2% (1.5-fold) increases respectively on comparison with MBTA.

Also as seen in Table 2, application of the compounds of the invention produced anthocyanin pigment content increases ranging from 43% to 104% compared to the control, 47% to 108% compared to DCPTA at the 1 ppm concentration, and 28% to 81% compared to MBTA at the 1 ppm concentration.

In sum, the activity at the low levels of 1 ppm and 0.1 ppm are unique to the compounds of the invention, in contrast to known plant bioregulators such as DCPTA and MBTA. Neither DCPTA nor MBTA produced responses greater than the control at 1 ppm. Some increases with DCPTA and MBTA over the control were observed at 10 ppm, but these were less than those with the compounds of the invention. The greatest increases were observed for 2-[N-methylbenzylaminoethyl]-4-methylbenzylether (NBMA).

TABLE 2

| Treatment | | Radish Plants | | |
| --- | --- | --- | --- | --- |
| | | Biomass | Root | Anthocyanin |
| Compound | ppm | Wet Wt (gm) | Wet Wt (gm) | Root: dry wt μg/g |
| IBTA | 10 | 55.4 ± 3.3 | 25.3 ± 1.8 | |
| IBTA | 1 | 57.7 ± 4.7 | 25.2 ± 2.3 | 6154 |
| PBTA | 10 | 49.5 ± 2.6 | 20.1 ± 2.4 | |
| PBTA | 1 | 51.1 ± 3.5 | 18.9 ± 2.0 | 5987 |
| NBIA | 10 | 59.0 ± 4.6 | 23.9 ± 1.5 | |
| NBIA | 1 | 54.0 ± 3.5 | 16.5 ± 1.3 | 6872 |
| NBMA | 1 | 72.9 ± 2.9 | 41.3 ± 4.0 | 7698 |
| NBMA | 0.1 | 70.2 ± 2.6 | 40.4 ± 2.8 | 7714 |
| NBDA | 10 | 57.5 ± 2.9 | 22.9 ± 1.1 | |
| NBDA | 1 | 48.4 ± 2.9 | 18.7 ± 1.6 | 5431 |
| NBPA | 10 | 46.1 ± 2.7 | 19.9 ± 1.8 | |
| NBPA | 1 | 44.7 ± 2.4 | 18.9 ± 1.4 | 5612 |
| DCPTA[1] | 10 | 41.8 ± 3.1 | 16.1 ± 1.1 | |
| DCPTA[1] | 1 | 36.9 ± 3.4 | 14.1 ± 1.9 | 3697 |
| MBTA[1] | 10 | 43.1 ± 2.1 | 17.3 ± 1.6 | |
| MBTA[1] | 1 | 37.1 ± 2.6 | 13.9 ± 1.8 | 4254 |
| Control | 0 | 37.7 ± 2.8 | 14.6 ± 1.2 | 3786 |

[1]Not in accordance with the invention. For comparison purposes only.

Example 5

This example describes bioregulator effects of the compounds of the invention on tomato plants.

Solutions of the hydrochloric acid salts of compounds IBTA, PBTA, NBIA, NBMA, NBDA, and NBPA containing 0.1% Kinetic™ nonionic wetting agent were prepared. Treatment rates were 10, 1, or 0.1 ppm active ingredient. Foliar application of the solutions were applied in a single application per treatment to young tomato [*Lycopersicum esculentum* cv. Pixie] seedlings at the early seedling (3–4 true leaf) stage by thoroughly drenching with the solutions until run off (approx. 10 ml solution/plant). Control plants were treated the same as the test plants except that no bioregulator compound was used. The solution applied to control plants was 0.1% Kinetic™. The plants were grown in the greenhouse in 2 gallon pots. The seeds were planted Mar. 26, 1993 and the fruits were harvested Jun. 21, 1993.

coloration, particularly in the flesh was seen in the fruits of the bioregulator-treated plants when compared to those of the untreated plants.

Responses appeared to be more uniform and consistent in the treated plants and greater variations were usually observed in the untreated control plants. The fruits of the treated plants matured earlier and were more uniform, and the desirable tomato flavor was more pronounced. The overall quality of the fruit appeared to be vastly improved. There was an increased yield of fruits due in part to increased branching and number of flowers. The fruits were usually larger. Balanced plant performances were observed without any negative imbalances. As shown in Table 4, similar results were observed on seed treatment.

TABLE 3

Tomato Plants

| Treatment | | Brix | Carotenoids | Fruit | | | |
|---|---|---|---|---|---|---|---|
| Cmp | ppm | % | μg/g fresh wt | total/plant | size g/fruit | % ripe | yield kg/plant |
| IBTA | 10 | 8.2 ± .04 | 186 ± 7 | 40 | 41 | 90 | 1.6 |
| IBTA | 1 | 7.9 ± .04 | 158 ± 4 | 35 | 39 | 88 | 1.4 |
| PBTA | 10 | 8.0 ± .04 | 182 ± 8 | 34 | 39 | 82 | 1.3 |
| PBTA | 1 | 6.0 ± .05 | 168 ± 6 | 40 | 36 | 78 | 1.5 |
| NBIA | 10 | 7.0 ± .03 | 160 ± 8 | 46 | 37 | 74 | 1.7 |
| NBIA | 1 | 7.2 ± .04 | 156 ± 9 | 46 | 37 | 72 | 1.7 |
| NBMA | 1 | 8.4 ± .04 | 191 ± 8 | 47 | 39 | 92 | 1.8 |
| NBMA | 0.1 | 7.3 ± .04 | 172 ± 7 | 38 | 40 | 89 | 1.5 |
| NBDA | 10 | 6.2 ± .07 | 152 ± 7 | 39 | 36 | 84 | 1.4 |
| NBDA | 1 | 6.4 ± .03 | 158 ± 6 | 40 | 35 | 77 | 1.4 |
| NBDA | 0.1 | 6.5 ± .04 | 150 ± 8 | 43 | 31 | 78 | 1.3 |
| NBPA | 10 | 5.8 ± .05 | 145 ± 7 | 38 | 28 | 71 | 1.1 |
| NBPA | 1 | 5.5 ± .06 | 137 ± 8 | 34 | 26 | 66 | 0.9 |
| Contl | 0 | 5.1 ± .04 | 78 ± 8 | 32 | 24 | 31 | 0.8 |

In another test, the bioregulator solutions were applied to tomato seeds. The seeds were soaked for 6 hours in solutions containing 0.1% Kinetic™. Treatment rates were 10, 1, or 0.1 ppm active ingredient. The seeds were planted after soaking and without prior drying. The plants were grown in the greenhouse in 2 gallon pots.

In both tests, the plants were observed for bioregulator effects. Fruit yield, fruit size, percent ripe fruit and yield per plants were measured. Determinations of Brix percent were made on fully ripe fruit. Brix was determined by a hand-held battery-operated digital refractometer already correlated to read Brix. Carotenoid content was determined on fully ripe fruit grown from treated seedlings by the usual method of taking a reading at 450 mμ of the extracted pigment solution in hexane using a spectrophotometer (Yokoyama et at., *Proceedings of the International Society of Citriculture* 3:717–722, (1977)). The results represent six replicate plants.

Results. Bioregulator activity of the compounds of the invention at low levels of concentration was observed. No residue of the bioregulators was detectable by HPLC after 2–3 weeks of application in the plant leaf or in the fruit which developed about 2–3 months later.

Table 3 shows the effects of the bioregulators on fruit quality and yield of tomato plants grown from treated seedlings. Significant increases in soluble solids content over control plants, as reflected in the Brix percentage results, were observed, accompanied by increases in carotenoid content. Due to the latter increase, improved

TABLE 4

Tomato Plants

| Treatment | | Brix | Fruit | | | yield |
|---|---|---|---|---|---|---|
| Cmp | ppm | % | total/plant | size g/fruit | % ripe | kg/plant |
| IBTA | 10 | 7.4 ± .04 | 38 | 39 | 89 | 1.5 |
| IBTA | 1 | 7.1 ± .05 | 31 | 36 | 85 | 1.4 |
| PBTA | 10 | 7.6 ± .06 | 32 | 35 | 84 | 1.1 |
| PBTA | 1 | 6.9 ± .03 | 39 | 37 | 80 | 1.4 |
| NBIA | 10 | 6.7 ± .05 | 37 | 41 | 79 | 1.6 |
| NBIA | 1 | 7.1 ± .05 | 41 | 40 | 82 | 1.7 |
| NBMA | 1 | 7.7 ± .06 | 47 | 39 | 83 | 1.8 |
| NBMA | 0.1 | 7.2 ± .04 | 41 | 36 | 81 | 1.5 |
| NBDA | 10 | 6.5 ± .07 | 36 | 32 | 83 | 1.3 |
| NBDA | 1 | 6.7 ± .06 | 37 | 31 | 84 | 1.4 |
| Contl | 0 | 5.2 ± .04 | 31 | 25 | 30 | 0.8 |

Example 6

The bioregulator effects of the compounds of the invention on spinach were determined. Foliar application of solutions of the hydrochloric acid salts of compounds IBTA, NBIA, NBMA, and NBDA (10 or 1 ppm active ingredient) with 0.1% Kinetic™ wetting agent were applied in a single application per treatment to spinach [Spinacea oleracea cv. New Zealand] at early seedling (2–3 leaf) stage to foliage runoff (approximately 20 ml/plant). Control plants were treated the same as the test plants except that no bioregulator compound was used. The solution applied to control plants was 0.1% Kinetic™.

The plants were grown in the greenhouse in 2 gallon pots and harvested 60 days after planting. Eight replicates were carried out. Biomass (whole plant) and chlorophyll (lead values were determined. Chlorophyll content was determined by the usual method of spectrophotometric readings.

Results. The results are tabulated in Table 5. Biomass was increased significantly over control plants. Total chlorophyll content was increased. The leaves appeared to be greener in coloration (reflecting the increase in the total chlorophyll content) and larger and more upright at a sharper angle.

TABLE 5

| Spinach | | | |
|---|---|---|---|
| Treatment | | Biomass | Chlorophyll total |
| Compound | ppm | dry wt gm | mg/g fresh wt |
| IBTA | 10 | 10.07 ± .31 | 1.98 ± .11 |
| NBIA | 10 | 10.21 ± .39 | 1.82 ± 1.2 |
| NBMA | 1 | 10.59 ± .43 | 1.69 ± .15 |
| NBDA | 10 | 10.10 ± .42 | 1.58 ± .14 |
| Control | 0 | 5.76 ± .65 | 1.28 ± .17 |

Example 7

The bioregulator effects of the compounds of the invention on barley were determined. Foliar application of solutions of the hydrochloric acid salts of compounds IBTA, PBTA, NBIA, NBMA, NBDA, and NBPA (10, 1, or 0.1 ppm active ingredient) containing 0.1% of Kinetic™ nonionic wetting agent were applied to foliage runoff (approximately 10 ml/plant) in a single application to robust barley (Hordeum vulgare L. cv. Robust) at early seedling stage shortly after germination (when the plants were about 6–10 cm tall). Control plants were treated the same as the test plants except that no bioregulator compound was used. The solution applied to control plants was 0.1% Kinetic™.

The plants were grown in the greenhouse, five plants per 1 gallon pot; six replicate pots per treatment. Plants were harvested at about 3 months. Bioregulator effects on the plants were observed.

Determinations of biomass and kernel weight were made. Kernel weight was determined as follows. Dry kernels separated from the spikes were collected for each of the barley plants, and weighed.

Results. Positive bioregulator responses were observed. The leaves of the treated plants were broader and longer, resulting, it is believed, in more efficient photosynthesis. As shown in Table 6, bioregulator treatment significantly increased the biomass weight and kernel weight compared to the control. Increases in kernel weight were a result of increases in the number of kernels per treated plant, that is, there were more kernels per "spike."

TABLE 6

| Barley | | | |
|---|---|---|---|
| Treatment | | Biomass | Kernels |
| Bioregulator | ppm | dry wt grm | dry wt grams |
| IBTA | 10 | 41.9 ± 2.1 | 12.6 ± .9 |
| IBTA | 1 | 52.7 ± 1.0 | 17.2 ± .8 |
| PBTA | 10 | 41.5 ± 0.8 | 12.9 ± .9 |

TABLE 6-continued

| Barley | | | |
|---|---|---|---|
| Treatment | | Biomass | Kernels |
| Bioregulator | ppm | dry wt grm | dry wt grams |
| PBTA | 1 | 38.5 ± 1.8 | 10.5 ± .5 |
| NBIA | 10 | 51.1 ± 1.3 | 17.1 ± .7 |
| NBIA | 1 | 52.6 ± 2.3 | 12.1 ± .9 |
| NBIA | 0.1 | 47.1 ± 2.3 | 13.8 ± .5 |
| NBMA | 10 | 52.1 ± 3.7 | 13.6 ± 1.0 |
| NBMA | 1 | 55.0 ± 2.5 | 15.5 ± .9 |
| NBMA | 0.1 | 56.6 ± 2.3 | 16.2 ± .8 |
| NBDA | 10 | 44.1 ± 2.6 | 12.9 ± .8 |
| NBDA | 1 | 46.5 ± 3.2 | 13.7 ± .9 |
| NBPA | 10 | 37.6 ± 3.9 | 11.1 ± .8 |
| NBPA | 1 | 35.7 ± 3.4 | 10.5 ± 1.0 |
| Control | 0 | 14.7 ± 0.8 | 6.2 ± .3 |

Example 8

The bioregulator effects of the compounds of the invention on corn (Zea mays L.) were determined. Solutions of the hydrochloric acid salts of the compounds IBTA, NBIA, NBMA, and NBDA at treatment rates of 10, 1, or 0.1 ppm active ingredient with 0.1% Kinetic™ nonionic wetting agent were applied in a single application as foliar applications to runoff (approximately 10 ml/plant) to corn [cv. Early Xtra-Sweet hybrid] at the early seedling stage shortly after germination when the plants were about 6–8 cm tall. Control plants were treated the same as the test plants except that no bioregulator compound was used. The solution applied to control plants was 0.1% Kinetic™.

The plants were grown in the greenhouse in 2 gallon pots; eight replicates per treatment, and harvested 2 months after planting. The plants were observed to assess differences between treated and control plants. Biomass was determined. The biomass results given in Table 7 represent only the stem (stalk) and leaf; roots are not included. At the stage of maturity of the corn plant when the biomass analysis was carried out, the corn had not fully matured, thus no corn cob and kernel weights are given.

Results. Biomass was increased significantly over control plants Gable 7). Additionally, in all of the numerous experiments conducted, the tassels always appeared before the silks, assuring good pollination for seed formation. This is valuable because one of the problems in the corn industry is poor pollination due to the silk appearing prior to tassel appearance, thus resulting in reduced seed formation and production. Further, the leaf structure was altered somewhat in that the leaf was longer and broader, having an impact on photosynthesis. Again, the unusual feature of the new bioregulators of the invention, particularly the compound 2-[N-methylbenzylaminoethyl]-4-methylbenzylether (NBMA), is their effectiveness at the extremely low concentration levels.

TABLE 7

| Corn | | |
|---|---|---|
| Treatment | | Biomass |
| Compound | ppm | dry wt (gm) |
| IBTA | 10 | 57.9 ± 3.4 |
| IBTA | 1 | 72.5 ± 2.3 |
| NBIA | 10 | 58.8 ± 3.1 |

TABLE 7-continued

Corn

| Treatment | | Biomass |
|---|---|---|
| Compound | ppm | dry wt (gm) |
| NBIA | 1 | 63.3 ± 2.3 |
| NBMA | 1 | 52.6 ± 2.5 |
| NBMA | 0.1 | 53.4 ± 1.5 |
| NBDA | 10 | 44.4 ± 2.1 |
| NBDA | 1 | 45.6 ± 1.3 |
| Control | 0 | 30.1 ± 3.4 |

Example 9

This example describes the bioregulator effects of the compounds of the invention on wheat (*Triticum aestivum durum* L.). Solutions of the hydrochloric acid salts of compounds IBTA, NBPA, NBIA, NBMA, and NBDA (10, 1, or 0.1 ppm active ingredient) containing 0.1% Kinetic™ nonionic wetting agent were applied in a single application as foliar application to runoff (approximately 10 ml/plant) to durum wheat at early seedling stage (4–6 cm tall). Control plants were treated the same as the test plants except that no bioregulator compound was used. The solution applied to control plants was 0.1% Kinetic™. The plants were grown in 2 gallon pots in the greenhouse, eight replicates per treatment and eight replicates for the control. The plants were harvested 2 months after planting. The yields of biomass (dry weight) and kernels (dry weight) were measured. The results are tabulated in Table 8.

In another test, the bioregulator solutions of IBTA, PBTA, NBIA, NBMA, and NBDA were applied to wheat seeds as a seed soak. Durum wheat seeds were soaked for 6 hours in the bioregulator solutions (10, 1, or 0.1 ppm active ingredient) containing 0.1% Kinetic™, and planted directly without drying. The plants were grown in 2 gallon pots in the greenhouse, 8 replicates. The plants were harvested 2 months after planting. Yields of biomass and kernels were measured. The results are tabulated in Table 9.

Results. The leaves of the treated plants were longer and broader. The total number of kernels per plant was increased significantly, indicative of yield increase response. As shown in Tables 8 and 9, application of the bioregulators of the invention significantly increased biomass and kernel weight compared to the controls.

TABLE 8

Wheat

| Treatment | | Biomass | Kernels |
|---|---|---|---|
| Compound | ppm | dry wt (gm) | dry wt (gm) |
| IBTA | 10 | 24.09 ± 1.23 | 9.97 ± 0.25 |
| IBTA | 1 | 34.56 ± 1.94 | 11.84 ± 0.64 |
| NBPA | 10 | 30.03 ± 2.82 | 9.94 ± 0.53 |
| NBPA | 1 | 34.92 ± 1.27 | 11.39 ± 0.58 |
| NBIA | 10 | 37.13 ± 2.88 | 12.15 ± 0.32 |
| NBIA | 1 | 40.40 ± 1.84 | 14.22 ± 0.50 |
| NBIA | 0.1 | 43.55 ± 1.57 | 15.21 ± 0.61 |
| NBMA | 10 | 35.88 ± 3.17 | 11.45 ± 0.63 |
| NBMA | 1 | 37.27 ± 2.10 | 11.69 ± 0.60 |
| NBDA | 10 | 32.58 ± 2.89 | 11.86 ± 0.36 |
| NBDA | 1 | 34.00 ± 0.89 | 11.91 ± 0.60 |
| Control | 0 | 17.23 ± 1.32 | 7.54 ± 0.73 |

TABLE 9

Wheat

| Treatment | | Biomass | Kernels |
|---|---|---|---|
| Compound | ppm | dry wt (gm) | dry wt (gm) |
| IBTA | 10 | 24.37 ± 1.46 | 9.75 ± 0.44 |
| IBTA | 1 | 27.02 ± 1.98 | 9.43 ± 0.76 |
| PBTA | 10 | 23.20 ± 1.22 | 6.93 ± 0.29 |
| PBTA | 1 | 28.39 ± 1.12 | 9.84 ± 0.61 |
| NBIA | 10 | 27.01 ± 1.04 | 9.40 ± 0.76 |
| NBIA | 1 | 28.41 ± 1.26 | 9.47 ± 0.60 |
| NBIA | 0.1 | 30.16 ± 1.12 | 10.18 ± 0.75 |
| NBMA | 10 | 31.75 ± 1.26 | 8.66 ± 0.60 |
| NBMA | 1 | 30.54 ± 1.25 | 9.74 ± 0.63 |
| NBMA | 0.1 | 25.85 ± 0.97 | 8.35 ± 0.41 |
| NBDA | 10 | 27.65 ± 1.86 | 9.82 ± 0.85 |
| NBDA | 1 | 28.61 ± 1.58 | 9.19 ± 0.42 |
| Control | 0 | 15.93 ± 0.61 | 6.72 ± 0.28 |

Example 10

This example describes the bioregulator effects of the compounds of the invention on grapes. A solution of the hydrochloric acid salt of the compound of the invention 2-[N-methylbenzylaminoethyl]-2-methylpropylether (NBIA) (10 ppm active ingredient) containing 0.1% Kinetic™ nonionic wetting agent was applied to field-grown Red Flame seedless grape [*Vitis vinifera* cv. Red Flame] vines grown in Coachella Valley, Calif. A single application to runoff was made shortly after shoots appeared in early spring (shoots were at 6–10 cm growth stage). For purposes of comparison, solutions of the acid salts of known bioregulators MBTA and DCPTA (10 ppm active ingredient) in 0.1% Kinetic™ were applied to Red Flame seedless grape vines the same as for the test bioregulator. Control plants were treated the same as the test plants except that no bioregulator compound was used. The solution applied to control plants was 0.1% Kinetic™.

Twenty kg samples of the test, comparison, and control grapes were harvested May 21, 1994, Jun. 5, 1994, and Jun. 15, 1994. The grape berries were separated from the stems, crushed, and aliquots of the grape juice analyzed for Brix percent. The visible spectra of water extracts of the anthocyanin pigments of the test, comparison, and control samples were obtained on a visible spectrophotometer.

Results. The application of the compound 2-[N-methylbenzylaminoethyl]-2-methylpropylether on vines of the Red Flame seedless grapes resulted in improving the overall quality of the berries. As shown in Table 10, the soluble solids content as reflected in the Brix readings was increased significantly, resulting in better tasting fruits with improved flavor. The bioregulator of the invention performed much better than MBTA or DCPTA. The color was also enhanced due to increased production of the anthocyanin pigments as shown in FIG. 1. A deeper enhanced red coloration of the berries and juices was observed.

TABLE 10

Grapes

| Harvest | | Brix % | | | |
|---|---|---|---|---|---|
| No. | Date | NBIA | MBTA[1] | DCPTA[1] | Control |
| 1st | May 21, 1994 | 15.9 | 15.2 | 15.0 | 15.1 |
| 2nd | June 5, 1994 | 19.9 | 18.7 | 17.6 | 17.1 |
| 3rd | June 15, 1994 | 22.8 | 20.2 | 19.5 | 18.2 |

[1]Not in accordance with the invention. For comparison purposes only.

Example 11

This example describes the bioregulator effects of the compounds of the invention on cantaloupe (*Cucumis melo* L. var. *cantalupensis* Naud.). Aqueous solutions of the hydrochloric acid salt of 2-[diethylaminoethyl]-2-methylpropylether (IBTA) (10 ppm active ingredient) containing 0.1% Kinetic™ wetting agent were applied to cantaloupe seeds by making the seeds for 6 hours. The control cantaloupe seeds were soaked with an aqueous solution of 0.1% Kinetic™ wetting agent for 6 hours. The seeds were planted in 3 gallon pots and grown in the greenhouse. After 4 months, the cantaloupes were harvested, cut in half, and observed for bioregulator effects.

Results. Treated cantaloupe showed thicker flesh and smaller seed cavity than the control. The color of flesh of the treated melon was visibly much deeper colored. This deeper orange coloration was due to increases in the carotenoid content.

Example 12

This example describes the bioregulator effects of the compounds of the invention on petunia (*Petunia hybrida* Velm.) floral plants. Solutions of the hydrochloride acid salt of 2-[N-methylbenzylaminoethyl]-4-methylbenzylether and 2-[N-methylbenzylaminoethyl]-2-methylpropylether (10, 1, 0.1, and 0.0125 ppm active ingredient) containing 0.1% Kinetic™ wetting agent were applied to petunia plants at early seedling (3–4 leaf stage) as foliar application until runoff (approximately 10 ml/plant). For comparison purposes solutions of DCPTA and MBTA (10, 1, 0.1, and 0.0125 ppm active ingredient) in 0.1% Kinetic™ were applied to petunia floral plants. The controls were seedlings treated with an aqueous solution of 0.1% Kinetic™ wetting agent. The plants were grown in 1 gal pots, 6 replicates. Greenhouse protocols called for the experimental pots to be arranged randomly on the table. Photos were taken when flowers started to appear and at or near full bloom.

Results. The petunia plant responses were visibly observed for responses and photos taken of the results. Positive bioregulator responses were observed at a level of concentration as low as 0.0125 ppm. Striking increases in anthocyanin color were visibly observed compared to the control. Neither DCPTA nor MBTA produced significant responses at the low level of 1 ppm and produced none at 0.1 or 0.0125 ppm. Reduced level of responses of DCPTA and MBTA were observed at 10 ppm when compared to the bioregulators of the invention at the same level of concentration. The foliage of the plants treated with the compounds of the invention was somewhat larger and more upright at a steeper angle than the controls.

Example 13

This example describes the bioregulator effects of the compounds of the invention on pansy (*Viola tricolor hortensis*) plants. Solutions of hydrochloric salt of 2-[N]-methylbenzylaminoethyl]-2-methylpropylether and 2-[N-methylbenzylaminoethyl]-4-methylbenzylether (0.0125, 0.1, 1, 10 ppm) with 0.1% Kinetic$^{TM}$ were applied as foliar applications to pansy seedlings (3–4 leaf stage). For comparison purposes, solutions of DCPTA and MBTA (0.0125, 0.1, 1, and 10 ppm) in 0.1% Kinetic™ were applied to pansy seedlings. Control seedlings were treated with aqueous solutions of 0.1% Kinetic™. The seedlings were grown in 1 gal pots, with 6 replicates.

Results. Similar responses to petunia floral plants were observed with pansies. Increases in anthocyanin coloration were observed visibly compared to the controls. Again, neither DCPTA or MBTA produced significant responses at the low level of 1 ppm and none at all at 0.1 or 0.0125 ppm as compared to the bioregulator compounds of the invention at the same concentration. The foliage of the plants treated with the compounds of the invention attained a deeper green coloration, indicative of increased accumulation of chlorophylls. The leaves were somewhat larger and broader.

Example 14

Mature (11 year old) citrus trees of Olinda Valencia orange (*Citrus sinensis* (L.) Osbeck) located at the Agricultural Experiment Station, University of California, Riverside, Calif. were used to test the effects of the compounds of the invention on citrus. Each treatment group contained four trees. The treatment groups consisted of the hydrochloric acid salts of the following: DCPTA –50 ppm; MBTA –50 ppm; 2-[N-methylbenzylaminoethyl]-2-methylpropylether (NBIA) –50 ppm; 2-[N-methylbenzylaminoethyl]-4-methylbenzylether (NBMA) –50 ppm. All solutions contained 0.1% Kinetic™ wetting agent. Control plants were treated the same as the test plants except that no bioregulator compound was used. Only a single application was made of each treatment. Four liters of a solution was applied to each tree to cover the entire foliage canopy shortly after fruit set. Fruit sizes ranged from 0.5 to 1.5 cm in fruit diameter. Randomly selected canopy mature fruits from four replicate trees were combined for fruit quality analysis. For analysis 10 fruits were selected from each treatment group. Total fresh fruit weight was determined. Peel thickness was determined on fruits cut in half. Fruits were juiced using an electric hand-juicer fitted with a 3 mm screen. The final juice volume and juice fresh weight were determined. Peel fresh weight after juicing and pulp fresh weight were determined. Juice samples were centrifuged at 25,000 xg for 15 minutes. The supernatant decanted and serum total soluble solids were determined using a hand-held battery-operated digital refractometer already corrected to Brix values. Vitamin C content was determined using a 2,6-dichloroindophenol titrimetric method of the Association of Official Analytical Chemists, 15th ed., 1990, Arlington, Va., 96721. Peel was separated from the endocarp (4 fruits) and freeze-dried. The carotenoid determination was carried out according to the usual method (H. Yokoyama et at., *Proceedings of the International Society of Citriculture* 3:717–722, (1977)).

Results. The results are presented in Tables 11 and 12. As shown in Table 11, significant increases in the fruit size were obtained using the compounds of the invention. In contrast, fruit treated with DCPTA and MBTA remained comparable to controls. The application of the compounds of the invention also caused increases in juice yield as reflected in ml juice per fresh fruit weight compared to the controls or to DCPTA or MBTA. The nutritional value of the fruit was enhanced as reflected in the increases in the vitamin C content of 33.3% for NBIA and 31.9% for NBMA over that of controls. The soluble solids increased, as shown in the Brix readings, of 39.6% for NBIA and 37.7% for NBMA over that of control. Peel thickness decreased by 14.3% for NBIA and 16.3% for NBMA, indicating an increase in the fruit endocarp, thus increase in the juice content.

On citrus fruits, NBIA and NBMA proved again to be superior performing compounds and outperformed both MBTA and DCPTA in providing more nutritious, higher soluble content and juicier fruits with thinner peels. For both NBIA and NBMA, juice yield increases of 8.2% over DCPTA and 6.0% over MBTA were observed. For NBIA, increases in vitamin C content of 22.4% over DCPTA and 15.4% over MBTA were observed; for NBMA, increases in vitamin C were 21.1% over DCPTA and 14.2% over MBTA. For NBIA, increases in soluble solids content, as reflected in Brix readings, were 20.3% over DCPTA and 16.5% over MBTA; for NBMA 18.7% over DCPTA and 15.0% over MBTA. Desirable thinner peels were observed for NBIA and NBMA: for NBIA, decreases in peel thickness of 10.9% over DCPTA and 6.8% over MBTA were observed, and for NBMA, decreases in peel thickness of 8.7% over DCPTA and 4.5% over MBTA were observed.

TABLE 11

Citrus

| Treatment 50 ppm | Fruit Diam mm | ml Juice/g fruit fresh wt | Vitamin C mg/100 ml | Serum Brix | Peel mm | Percent of Fruit juice fresh wt | peel + pulp fresh wt |
|---|---|---|---|---|---|---|---|
| NBIA | 65.4 a[1] | 0.53 a | 56.8 a | 14.8 a | 4.1 b | 51.9 a | 46.9 a |
| NBMA | 65.2 a | 0.53 a | 56.2 a | 14.6 a | 4.2 b | 51.8 a | 46.7 a |
| DCPTA[2] | 64.1 b | 0.49 b | 46.4 b | 12.3 a | 4.6 b | 51.4 a | 47.1 b |
| MBTA[2] | 64.0 b | 0.50 b | 49.2 b | 12.7 a | 4.4 b | 51.5 a | 47.1 b |
| Control | 63.9 b | 0.49 b | 42.6 c | 10.6 b | 4.9 a | 50.7 b | 47.4 b |

[1]Means associated with the same letter are not significantly different, according to Duncan's multiple range tests [P >5%].
[2]Not in accordance with the invention. For comparison purposes only.

Visual observations indicated that both endocarp and flavedo of treated fruits exhibit enhanced coloration with NBIA and NBMA showing somewhat deeper enhancement. These observations are confirmed in Table 12. As can be seen from the data, increased pigmentation was observed in both peel and endocarp on application of NBIA and NBMA. In the endocarp, NBIA and NBMA increased the carotenoid content 71% and 44%, respectively, over the controls. Again, both NBIA and NBMA proved superior to either DCPTA or MBTA. NBIA increased carotenoid content 53% over DCPTA and 22% over MBTA. NBMA increased carotenoid content 43% over DCPTA and 20% over MBTA. In the peel, NBIA increased carotenoid content by 62% and NBMA by 41% over controls. Increased carotenoid contents were observed for NBIA of 62% and for NBMA of 41% over the controls. On comparison with DCPTA and MBTA, NBIA showed increases of 47% over DCPTA and 44% over MBTA; NBMA showed increases of 28% over DCPTA and 25% over MBTA.

TABLE 12

| | Carotenoid Content (μg/g dry wt) | |
|---|---|---|
| Treatment | Endocarp | Peel |
| NBIA | 266 | 302 |
| NBMA | 224 | 263 |
| DCPTA[1] | 174 | 205 |
| MBTA[1] | 186 | 210 |
| Control | 156 | 186 |

[1]Not in accordance with the invention. For comparison purposes only.

Example 15

A large candelilla plant (*Euphorbia antisiphylitica* Zucc.) was selected from Teralingua, Tex., and cuttings were grown in the greenhouse at the University of California at Riverside. After one year of growth, these cuttings were treated with the novel plant bioregulators at several levels of concentration. The wetting agent used was Kinetic™ at 0.1% w/v.

Six months after treatment the stems were harvested. At harvest time the stems were cut 2 cm. above ground and extracted with chloroform for 5 min. three times. The combined extracts and the extracted stems were dried and weighed and the yield of the raw wax expressed as a percentage; dry wt wax g/dry tissue stems g.

Results. As shown in Table 13, significant increases in wax yield at the 1.0 and 10 ppm levels were observed in Candelilla plants treated with 2-[N-methylbenzylaminoethyl]-2-methylpropylether (NBIA). Significant increase in wax yield was observed at the lower level of concentration 0.05 ppm in plants treated with 2-[N-methylbenzylaminoethyl]-4-methylbenzylether (NBMA).

TABLE 13

| Treatment | Concentration ppm | Wax Yield %[1] |
|---|---|---|
| Control 0.1% Kinetic ™ | 0 | 2.83 a |
| NBIA | 0.1 | 3.01 ab |
| NBIA | 1.0 | 3.37 bc |
| NBIA | 10.0 | 3.50 c |
| NBMA | 0.05 | 3.57 c |
| NBMA | 1.0 | 2.76 a |

[1]Duncan's Multiple Range Test was used to separate the means.

Example 16

This example describes the effects of the compounds of the invention on yew plants. Aqueous solutions of the hydrochloric acid salts of 2-[diethylaminoethyl]-2-methylpropylether (IBTA) and 2-[N-methylbenzylaminoethyl]-2-methylpropylether (NBIA) having 10 and 1 ppm active ingredient and containing 0.1% Tween 80 wetting agent were prepared. For purposes of comparison, solutions of 10 and 1 ppm DCPTA containing 0.1% Tween 80 wetting agent were prepared. The control solution contained only 0.1% Tween 80 wetting agent. Roots of rooted cuttings of yew plants *Taxus brevifolia* and *T.* sp. x *media* cv. Hicksii were soaked for 20 minutes in the test, comparison, and control solutions before transplanting. The plants were grown in 2 gallon pots outdoors under a sunscreen in Pasadena, Calif. Shortly after the appearance of new growth, the test plants were treated with 1 ppm active ingredient foliar application until runoff. Controls were treated with the control solution until runoff. The plants were harvested 40 weeks after the initial treatment. Yields of biomass and taxol content were determined. Biomass yield was determined as the average dry weight of whole plants including needles; 4 plants. Taxol content was determined as the average taxol content of stems of whole plants stripped of needles; 4 plants. Taxol content was determined by the method of N. Vidensek et al.,(N. Videnesek, P. Lee, A. Campbell, and C. Carlson, *J. Natural Products* 53:1609–1610 (1990)).

Results. The compounds of the invention significantly increased the yields of biomass and taxol content compared to DCPTA-treated plants or the control. Increases over the control ranged from 112% to 175% increases in taxol content and 33% to 41% increases in biomass. The results are tabulated in Table 14.

TABLE 14

Yew Plants

| Treatment | Taxol Content (% dry wt.) | | Biomass (gm dry wt) | |
|---|---|---|---|---|
| | *T. brevifolia* | *T.* sp. x *media* cv Hicksii | *T. brevifolia* | *T.* sp. x *media* cv Hicksii |
| IBTA | 0.017 ± .001 | 0.009 ± .001 | 56.8 ± 2.3 | 41.7 ± 1.7 |
| NBIA | 0.021 ± .001 | 0.011 ± .001 | 60.1 ± 2.4 | 43.9 ± 2.2 |
| DCPTA[1] | 0.011 ± .001 | 0.005 ± .001 | 47.3 ± 2.6 | 35.7 ± 2.2 |
| Control | 0.008 ± .001 | 0.004 ± .002 | 42.8 ± 2.3 | 31. 1± 1.6 |

[1]Not in accordance with the invention. For comparison purposes only.

The yew plant (*Taxus baccatta*) was treated with an aqueous solution of the hydrochloric acid salt of 2-[N-methylbenzylaminoethyl]-2-methylpropylether (NBIA) (10 ppm) as a seedling root soak (15 rain) prior to transplanting. The wetting agent was 0.1% Kinetic™. The control plant was treated with a solution of 0.1% Kinetic™.

Figure 2:
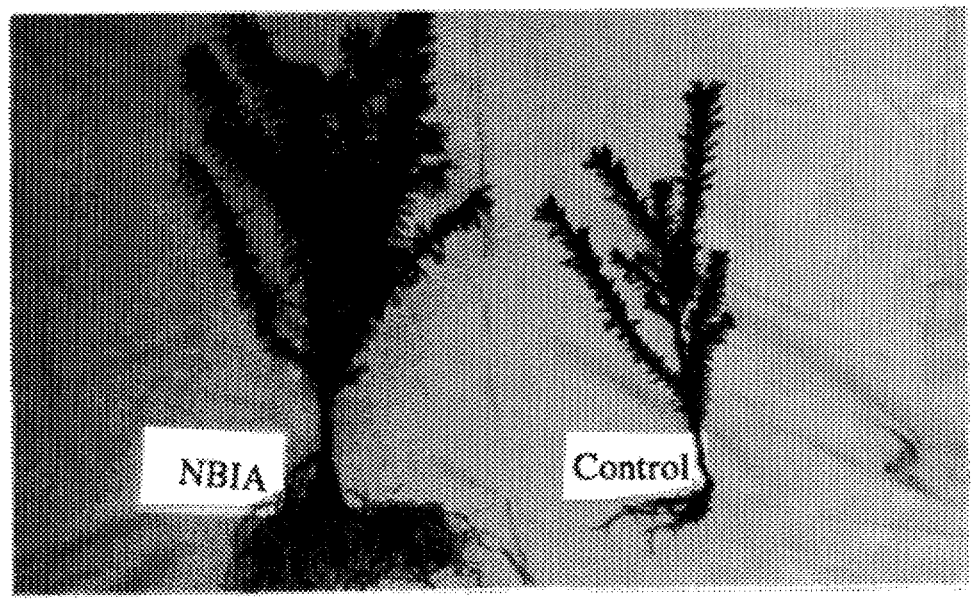
FIG. 2 shows the effect of the compound 2-[N-methylbenzylaminoethyl]-2-methylpropylether (NBIA) on the yew (Taxus spp.) plant. The treated plant is on the left and the control plant is on the right.

Results. As shown in FIG. 2, the yew plant treated with the novel bioactive compound of the invention (on the right in the figure) showed significantly greater biomass compared to the control plant (on the left).

Example 17

This example describes the effects of selected compounds of the invention on plants treated with the compounds and exposed to sucking insects.

Tomato seeds were soaked for 6 hours in aqueous solutions of the hydrochloric acid salt of 2-[diethylaminoethyl] -2-methyl-2-phenylpropylether (PBTA) or 2-[diethylaminoethyl]-2-methylpropylether (IBTA) (10 ppm active ingredient) containing 0.05% Tween 80 wetting agent. Control seeds were treated with 0.05% Tween 80.

Seeds were planted Jul. 15, 1992 and grown in the greenhouse. After germination, the test and control plants were exposed to continuous populations of the silverleaf whitely [*Bemisia argentifolii* Bellows and Perring] which is a "sucking insect" from Jul. 29, 1992. Plants were harvested Sep. 2, 1992. Each treatment had nine replications.

Results. Plants treated with 2-[diethylaminoethyl]-2-methyl-2-phenylpropylether showed resistance to the silverleaf whitely (sucking insect), whereas plants treated with 2-[diethylaminoethyl]-2-methylpropylether did not. The results are shown in Table 15. The leaf area index (LAI) data gives an indication in relative number of nymphs reduced by treatment of plants. The addition of a phenyl group to the isobutyl moiety is the structural difference between the two compounds. These results were totally unexpected. No anti-insect properties were observed in previous experiments with DCPTA or MBTA.

TABLE 15

| Tomato Plants | | | |
|---|---|---|---|
| Treatment | | *B. argentifolii* | Nymphs |
| Compound | ppm | per leaf | LAI[1] × 1000 |
| IBTA | 10 | 134.7 ns | 18.5 ab[2] |
| PBTA | 10 | 107.6 | 15.5 b |
| Control | 0 | 120.7 | 21.6 ab |

[1]LAI = leaf area index measured in cm$^2$ by a LiCOr® Portable Area Meter.
[2]Means associated with the same letter are not significantly different (P <0.05).

Example 18

This example describes the effects of 2-[diethylaminoethyl]-2-methylpropylether on plants treated with the compound and exposed to chewing insects.

Young seedlings of cantaloupes (*Cucumis melo* L. var. *cantalupensis* Naud.), cabbages (*Brassica oleracea* L.), and cucumbers (*Cucumis sativus* L.) were treated with 2-[diethylaminoethyl]-2-methylpropylether (IBTA) by foliage application to runoff of an aqueous solution of the hydrochloric acid salt of IBTA (10 ppm active ingredient) containing a 0.1% Kinetic™ wetting agent. Control plants were seedlings treated with an aqueous solution of 0.1% Kinetic™ wetting agent. The treated and control plants were grown outdoors and there was a heavy infestation of chewing insects.

Figure 3:
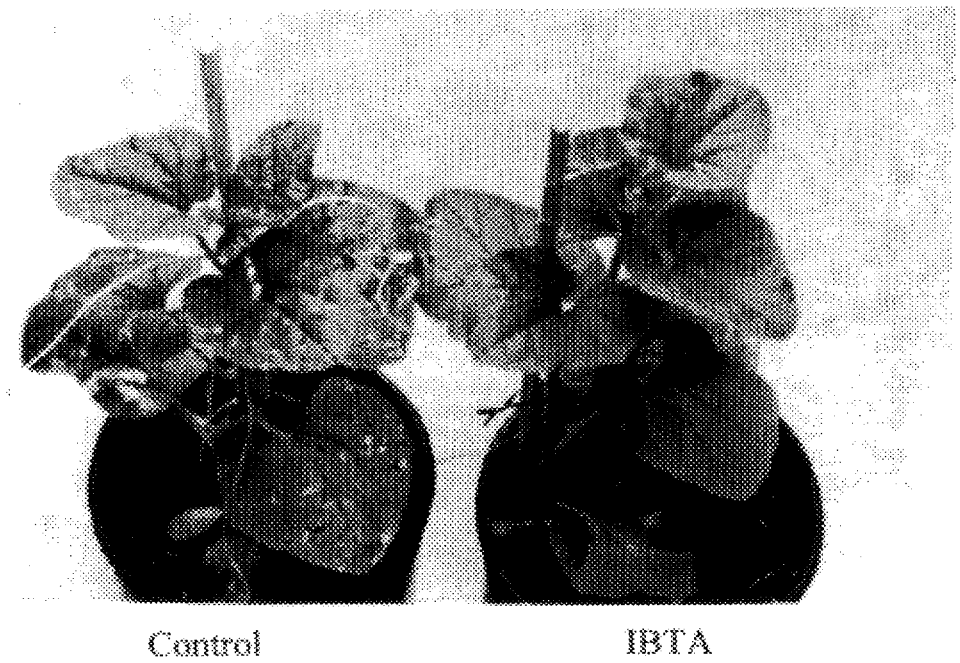
FIGS. 3 shows the effect of the compound 2-[diethylaminoethyl]-2-methylpropylether (IBTA) in eliciting resistance in plants to chewing insects. The control plant is on the left and the treated plant is on the right.

Results. All the leaves of the control plants were heavily damaged by the chewing insects whereas the leaves of the treated plants remained virtually undamaged. FIG. 3 shows the effects of IBTA on cantaloupe plants 30 days after foliar application. As can be seen in the figure, significant insect damage occurred on the control plant (on the left in the figure), whereas virtually no damage occurred on the treated plant (on the right). As discussed above, this compound had no effect against sucking insects. No anti-insect properties were observed in previous experiments with DCPTA or MBTA.

What is claimed is:

1. A compound selected from the group having the structure

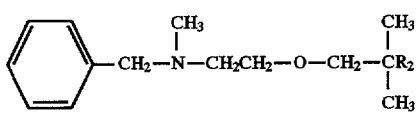

wherein $R_2$ is methyl; and (b) an acid addition salt thereof.

2. A compound selected from the group having the structure

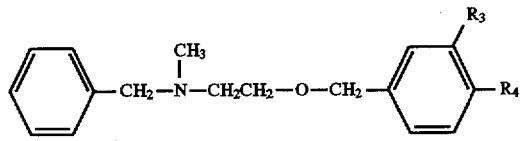

wherein $R_3$ and $R_4$ are in the meta and para positions, respectively, on the ring, and wherein $R_3$ is methyl and $R_4$ is hydrogen or methyl, or wherein $R_3$ and $R_4$ are both chlorine; and (b) an acid addition salt thereof.

3. The compound of claim 2 wherein $R_3$ is methyl and $R_4$ is hydrogen.

4. The compound of claim 2 wherein $R_3$ and $R_4$ are methyl.

5. A compound selected from the group having the structure

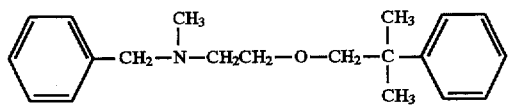

and (b) an acid addition salt thereof.

6. A method for enhancing plant growth, comprising applying to a plant a compound selected from the group consisting of:

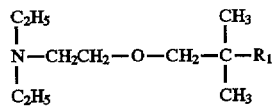

wherein $R_1$ is phenyl;

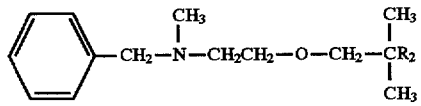

wherein $R_2$ is hydrogen or methyl;

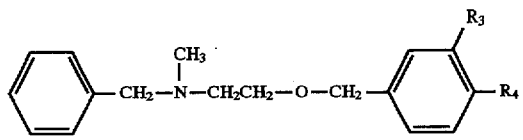

wherein $R_3$ and $R_4$ are in the meta and para positions, respectively, on the ting, and wherein $R_3$ is hydrogen or methyl find $R_4$ is methyl, or wherein $R_3$ and $R_4$ are both chlorine;

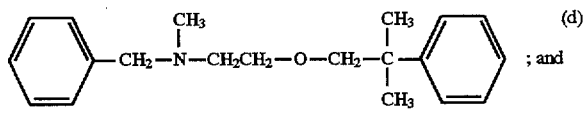

(e) an acid addition salt of compounds (a)–(d);

said compound being applied to the plant immediately prior to or at a time when cell differentiation and growth of the plant or flower buds are great, that is, to seeds, to plant seedlings, or to trees during flower bud initiation, bud swell or during a period of exponential vegetative growth, said compound being applied to the plant in an effective bioregulatory amount, this is, an amount sufficient to enhance plant growth but insufficient to inhibit plant growth, said enhancing of plant growth consisting of an increase in total plant biomass and plant constituents selected from the group consisting of protein, lipid, sugar, and essential oil.

7. The method of claim 6 wherein the enhancing of plant growth further consists of an accelerated structural maturation of the plant and reduction of days to crop harvest compared to an untreated plant.

8. The method of claim 6 wherein the enhancing of plant growth further consists of an increase in plant constituents selected from the group consisting of pigment, soluble solids, vitamin content, and juice content.

9. The method of claim 6 wherein the compound is 2-[diethylaminoethyl]-2-methyl-2-phenylpropylether, 2-[N-methylbenzylaminoethyl]-2-methylpropylether, 2-[N-methylbenzylaminoethyl]-4-methylbenzylether, 2-[N-methylbenzylaminoethyl]-3,4-dimethylbenzylether, 2-[N-methylbenzylaminoethyl]-2-methyl-2-phenylpropylether, or acid addition salt thereof.

10. The method of claim 6 wherein the plant is a dicot.

11. The method of claim 6 wherein the plant is a monocot.

12. The method of claim 6 wherein the plant is a floral plant.

13. A method of increasing the content of taxol in a yew plant, comprising applying to a yew plant a compound selected from the group consisting of 2-[N-methylbenzylaminoethyl]-4-methylbenzylether, N-methyl-2-benzylaminoethyl-4-methylbenzylether, 2-[N-methylbenzylaminoethyl]-3,4-dimethylbenzylether, 2-[N-methylbenzylaminoethyl]-3,4-dichlorobenzylether, or acid addition salt thereof, said compound being applied to the plant at an early stage of plant development, that is, to the seed, to a plant seedling or plant part, said compound being applied to the plant in an amount effective to increase taxol in the plant compared to an untreated yew plant.

14. A method of causing a plant to become resistant to sucking insects, comprising applying to a plant 2-[diethylaminoethyl]-2-methyl-2-phenylpropylether or acid addition salt thereof, said compound being applied to the plant in an amount effective to cause the plant to become resistant to sucking insects compared to an untreated plant.

* * * * *